United States Patent
Woods et al.

(10) Patent No.: US 10,314,555 B1
(45) Date of Patent: Jun. 11, 2019

(54) APPARATUS TO TRANSLATE TWO-DIMENSIONAL PLANAR POSITIONS INTO THREE-DIMENSIONAL FIXED RADIAL POSITIONS

(71) Applicant: Amazon Technologies, Inc., Seattle, WA (US)

(72) Inventors: David Lyle Woods, Concord, NH (US); Jon Joseph Varteresian, Hubbardston, MA (US); Andrew Waddell Boone, Windham, NH (US)

(73) Assignee: Amazon Technologies, Inc., Seattle, WA (US)

( * ) Notice: Subject to any disclaimer, the term of this patent is extended or adjusted under 35 U.S.C. 154(b) by 42 days.

(21) Appl. No.: 15/795,010

(22) Filed: Oct. 26, 2017

(51) Int. Cl.
*G01B 11/26* (2006.01)
*A61B 6/00* (2006.01)
*A61B 6/02* (2006.01)

(52) U.S. Cl.
CPC .................. *A61B 6/44* (2013.01); *A61B 6/02* (2013.01); *A61B 6/4085* (2013.01);
(Continued)

(58) Field of Classification Search
CPC .... G01B 11/24; G01B 11/306; G01B 21/042; G01B 11/03; G01B 5/008; G01B 15/00; G01B 11/2433; G01B 15/04; G01B 3/30; G01B 9/02039; G01B 9/02057; G01B 9/0209; G01B 11/2441; G01B 21/045; G01B 2290/25; G01B 9/02072; G01B 11/002; G01B 5/012; G01B 11/007; G01B 11/026; G01B 11/14; G01B 11/245; G01B 11/25; G01B 11/255; G01B 11/303; G01B 15/045; G01B 21/00; G01B 21/20; G01B 3/00; G01B 5/00; G01B 5/0014; G01B 5/016; G01B 9/02083; G01J 9/00; G01J 3/46; G01J 3/463; G01J 3/508; G01J 1/0242; G01J 1/04; G01J 1/0403; G01J 2003/2866; G01J 3/28; G01J 3/2823; G01N 2223/419; G01N 23/046;
(Continued)

(56) References Cited

U.S. PATENT DOCUMENTS

2005/0166413 A1* 8/2005 Crampton .............. B25J 13/088
33/503
2006/0023222 A1* 2/2006 Binder ...................... G01J 1/04
356/446
(Continued)

*Primary Examiner* — Michael P Stafira
(74) *Attorney, Agent, or Firm* — Kilpatrick Townsend & Stockton LLP (57) ABSTRACT

An apparatus includes a base. The base includes a first mount configured to receive a first device. First and second guides overlap each other, are each pivotally coupled with the base, and each include an arcuate body. The chassis is received by the first guide and the second guide so as to be configured for sliding along the first guide and the second guide. The chassis includes a second mount for receiving a second device for movement of the second device between a first set of points defining a reference spherical cap relative to the base. A member may be provided between the chassis and an actuator operable to move among a set of points defining a reference plane so as to cause movement of the chassis among another set of points defining a reference spherical cap about the first mount for the first device.

12 Claims, 5 Drawing Sheets

(52) U.S. Cl.
CPC ............ *A61B 6/4208* (2013.01); *A61B 6/488* (2013.01); *A61B 6/582* (2013.01); *A61B 6/4266* (2013.01); *G01B 11/26* (2013.01)

(58) Field of Classification Search
CPC ... G01N 2223/1006; G01N 2223/3306; G01N 23/083; G01N 21/9515; G01N 15/1429; G01N 15/1456; G01N 2015/1454; G01N 2021/4707; G01N 2021/8812; G01N 21/41; G01N 21/4133; G01N 21/453; G01N 21/8806; G01N 21/8806; G01N 2201/0612; G01N 2201/08; G01N 2021/1793; G01N 2021/1797; G01N 21/274; G01N 21/31; G01N 21/9503; G01N 29/04; G01N 29/0681; G01N 29/221; G01N 29/2418; G01N 29/46; G02B 21/006; G02B 23/2446; G02B 23/2461; G02B 23/26; G02B 27/0025; G02B 21/361; G02B 5/32; G02B 6/102

See application file for complete search history.

(56) References Cited

U.S. PATENT DOCUMENTS

| | | | | |
|---|---|---|---|---|
| 2011/0258867 | A1* | 10/2011 | McDonnell | G01B 5/008 33/502 |
| 2015/0355113 | A1* | 12/2015 | Christoph | G01B 15/00 378/4 |
| 2017/0363403 | A1* | 12/2017 | Jonas | G01B 5/0014 |
| 2017/0370690 | A1* | 12/2017 | Held | G01B 5/012 |
| 2018/0094913 | A1* | 4/2018 | Held | G06T 7/73 |

* cited by examiner

APPARATUS TO TRANSLATE TWO-DIMENSIONAL PLANAR POSITIONS INTO THREE-DIMENSIONAL FIXED RADIAL POSITIONS

BACKGROUND

Sensors and detectors are used for a variety of applications. Information related to such devices is often processed based on prior testing of the devices within controlled conditions. In many situations, accuracy of information can be improved by reference to more precise control conditions. However, especially for devices that provide or obtain readings from within a three dimensional space, calibration or testing can be difficult as a result of difficulties in precisely or accurately representing sources of information within a three dimensional space.

BRIEF DESCRIPTION OF THE DRAWINGS

Various embodiments in accordance with the present disclosure will be described with reference to the drawings, in which.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Techniques described herein include use of an actuator arrangement of one or more actuators to navigate to a two-dimensional point in a plane. The actuator arrangement may be part of—or coupled with—a rig or apparatus so that navigating to the two-dimensional point in the plane will cause (e.g., through appropriate linkages or other mechanical elements of the assembly) another part of the apparatus to navigate to a point along a portion of a sphere. Thus, a device (e.g., an emitter) placed at the center of the spherical shape can be tested or calibrated based on movement of a corresponding device (e.g., a receiver, sensor, deflector, or reflector) along the surface of the spherical shape in response to the movement or navigation along the plane provided by the actuator arrangement. Alternatively, the device that travels along the sphere may be tested or calibrated based on information from the centrally-located device. More generally, the apparatus may move a transmitter or detector to different fixed radial positions relative to a device at the center of the reference spherical shape, e.g., to test or calibrate either or both of the centrally-located device or the travelling device.

Apparatuses that utilize an actuator arrangement to navigate to two-dimensional points instead of using actuators that must navigate to three-dimensional points may allow for much greater simplicity when obtaining data for improved calibration of devices. For example, a less complex actuator arrangement may be used to obtain such data. In many cases, two-dimensional actuators or actuators that are capable in moving in two dimensions may be used to provide an end result of a set of three-dimensional target positions without having to resort to use of more complex three-dimensional actuators to reach the three-dimensional positions.

In an example embodiment, the actuator corresponds to a motion controller device having two axes of controlled movement for positioning along or among points in a plane. The actuator is capable of moving a housing within the plane. A ball joint is located within the housing. The ball joint is connected with an elongate member that extends toward a set of guides. The set of guides includes two guides arranged perpendicularly to one another. Each of the guides is semi-circular in shape and includes a slot along the length of the guide. The guides are each attached by hinges to a base that holds a device to be tested. The hinges allow each guide to pivot through an arc relative to the device to be tested. For example, one of the guides may be arranged to pivot between different longitudinal lines relative to the device to be tested, while the other of the guides may be arranged to pivot between different latitudinal lines relative to the device to be tested. The guides overlap one another so that the pivoting of each guide is not obstructed by the pivoting of the other guide. For example, one of the guides may be positioned slightly inwardly or outwardly of the other so that both can freely pivot without running into or otherwise interfering with each other. The end of the elongate member that extends away from the ball joint and toward the guides also engages with the guides so that movement is constrained to follow the pivoting motion of the guides. For example, the end of the member engaged with the guides may include a chassis or be coupled with a chassis that extends through the slot in each one of the guides. Due to the member being positioned between the guides and the ball joint, movement caused by the actuator to move among positions within the plane is translated via the member into motion of the other end of the member or the chassis along positions on a hemisphere defined by the semi-circular guides. In this way, a testing device mounted on the chassis can be moved among different positions at a fixed radius away from the device to be tested, and such movement may be accomplished by the relatively simple actuator arrangement that is capable of moving in two axes rather than in additional degrees of freedom. The testing device may also remain facing the device to be tested, e.g., which may be facilitated by using a non-circular cross-section in the portion of the chassis that extends through the slots in the guides such that motion will be constrained to translation without twisting or rotation in the guides.

Figure 1:
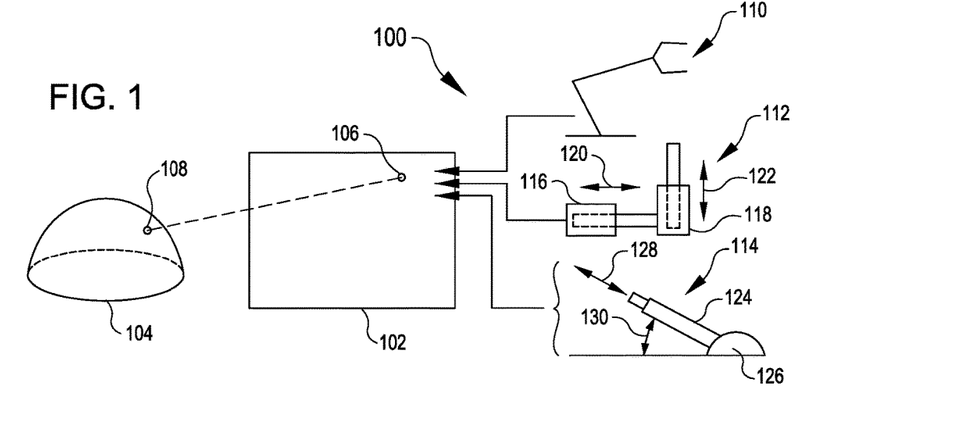
FIG. 1 illustrates various examples of actuators that can be utilized for navigating within a plane in a manner that can be translated by suitable structure for providing navigation to positions along a spherical cap in accordance with various embodiments.

FIG. 1 illustrates various examples of actuators 100 that can be utilized for navigating within a plane 102 in a manner that can be translated by suitable structure for providing navigation to positions along a spherical cap 104. For example, each one of the actuators 100 may be capable of navigating within the plane 102 or reaching a planar point 106 therein, which may be converted to a spherical point 108 on the reference spherical cap 104 by structure such as will be described further herein with respect to later figures.

The spherical cap 104 is depicted in FIG. 1 as a hemisphere, although embodiments herein are not so limited. For example, the spherical cap 104 can correspond to any portion of a shape that includes a spherical or arcuate surface, including, but not limited to, a truncated portion of a sphere, an end portion of a sphere, or other portion of a sphere. The spherical cap 104 may be defined by a first set of points. The first set of points defining the spherical cap may be defined at least in part by motion of other elements described herein with respect to other figures below.

The actuators 100 in FIG. 1 can be suitably coupled with any appropriate computer or set of computers for controlling operation, which may include, but are not limited to, those described with respect to FIG. 7 below. Non-limiting examples of the actuators 100 include a robotic arm 110, a bi-axis actuator 112, and an angularly extendible actuator 114.

In some aspects, an actuator 100 (e.g., robotic arm 110) may be utilized that has more degrees of freedom than the two degrees of freedom that would provide navigation within a plane 102. In such cases, the extra degrees of freedom may be disabled or otherwise not used in order to simplify operation for achieving navigation within the plane 102.

In some embodiments, the bi-axis actuator 112 can correspond to a motion controller having two axes of controlled movement. The bi-axis actuator 112 is illustrated with linear actuators 116 and 118, for example, that are respectively capable of movement in a first (e.g., horizontal) direction 120 and a second (e.g., vertical) direction 122. However, the direction provided by the linear actuators 116 and 118 need not necessarily be perpendicular to one another.

The angularly extendable actuator 114 is illustrated as an assembly having a length-adjustable actuator 124 and an angle-adjustable actuator 126. For example, such elements may respectively enable changes along a length direction 128 to change a magnitude of the actuator and enable changes in an angular position 130 to change an orientation of the angularly extendible actuator 114, similar to adjusting a direction and magnitude of a vector.

Figure 2:
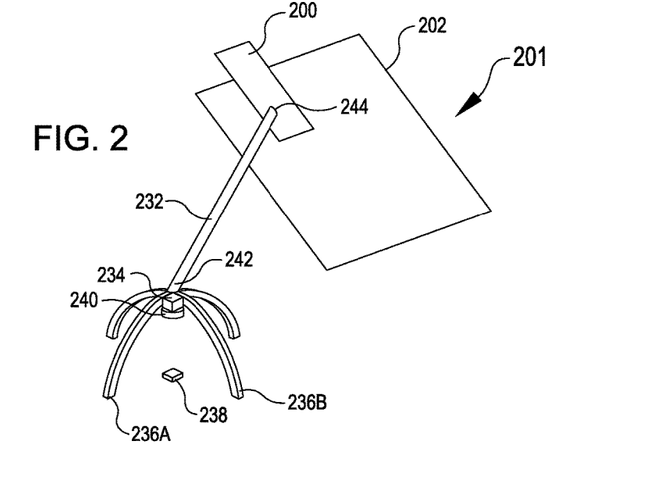
FIG. 2 is a schematic diagram of elements of a system for translating between positions in accordance with various embodiments.

FIG. 2 is a schematic diagram of elements of a system 201 for translating between positions according to certain embodiments herein. Various elements depicted in FIG. 2 are shown and described schematically or functionally with some options for specific details described and/or shown later on.

The system 201 depicted in FIG. 2 includes an actuator 200 (which may be an example of the actuator 100), a member 232, a chassis 234, guides 236 (individually identified as a first guide 236A and a second guide 236B), a first or fixed device 238, and a second or traveling device 240. The member 232 includes a first end 242 coupled with the chassis 234 and a second end 244 coupled with the actuator 200. In operation, the actuator 200 can move among positions within the plane 202, similar to planar motion described by actuators 100 with respect to plane 102 in FIG. 1. Movement of the actuator 200 can thus move the second end 244 of the member 232, which can in turn cause movement of the first end 242 of the member 232.

The chassis 234 can be coupled with or form a part of the first end 242 of the member 232 such that the chassis 234 moves in response to movement by the actuator 200. The chassis 234 may be received by or through the guides 236 such that the guides 236 constrain, affect, and/or direct the motion of the chassis 234 that occurs in response to the movement of the actuator 200 relative to the plane 202. For example, the chassis 234 may be arranged or configured for sliding along the guides 236.

The guides 236 may each be hinged. The second guide 236B may overlap the first guide 236A such that both guides 236 are permitted to respectively pivot in conjunction with one another, but without necessarily obstructing pivoting by one another. For example, the first guide 236A may be positioned inwardly or outwardly of the second guide 236B.

The fixed device 238 can be fixed in place relative to the hinges or other anchor points of the guides 236. For example, the fixed device 238 may be mounted via a first mount for receiving the fixed device 238.

The traveling device 240 may be coupled with the chassis 234 so as to move with the chassis 234. For example, the chassis 234 may correspond to or include a second mount for receiving the traveling device 240. In operation, the traveling device 240, the chassis 234, and/or the first end 242 of the member 232 may move among points that are among a first set of points that define a spherical cap about the fixed device 238 (e.g., similar to the spherical cap 104 of FIG. 1). For example, the motion or movement among the first set of points defining the reference spherical cap may occur in response to movement that the actuator 200 provides among a second set of points that defines the reference plane 202.

The fixed device 238 and the traveling device 240 may correspond to respective devices of a pair of devices that include an emitting device and a corresponding receiving device capable of receiving or detecting emissions from the emitting device. Examples of suitable pairs of devices include a pair with a speaker and a microphone, a pair with a sound emitter and sound receiver, a pair with a non-laser heat emitter and a heat detector, a pair with an emitter of non-visible electromagnetic radiation and a receiver of such non-visible electromagnetic radiation, or a pair with a laser and laser-receiving device.

As an illustrative example, the fixed device 238 may correspond to a speaker that is to be tested by the use of a microphone as the traveling device 240. Alternatively, the fixed device 238 could be a microphone to be tested by a traveling device 240 that corresponds to a speaker that can be moved among different fixed radial positions relative to the microphone, such as to provide data for testing the ability of the microphone to pick up signals from different angles or for testing the strength or other characteristics of such signals received from such different orientations. More generally, for a pair that includes an emitter and a receiver, relative arrangements of the system 201 can include either where the emitter is the fixed device 238 and the receiver is the traveling device 240 or where the receiver is the fixed device 238 and the emitter is the traveling device 240.

In some embodiments, the member 232 may correspond to a variable length member. Non-limiting examples of a variable length member can include an extendable member, a telescoping rod, or an extension spring. In some embodiments, the member 232 being a variable length member may allow for changes in length that accommodate constraints provided by the actuator 200 and the guides 326.

Figure 3:
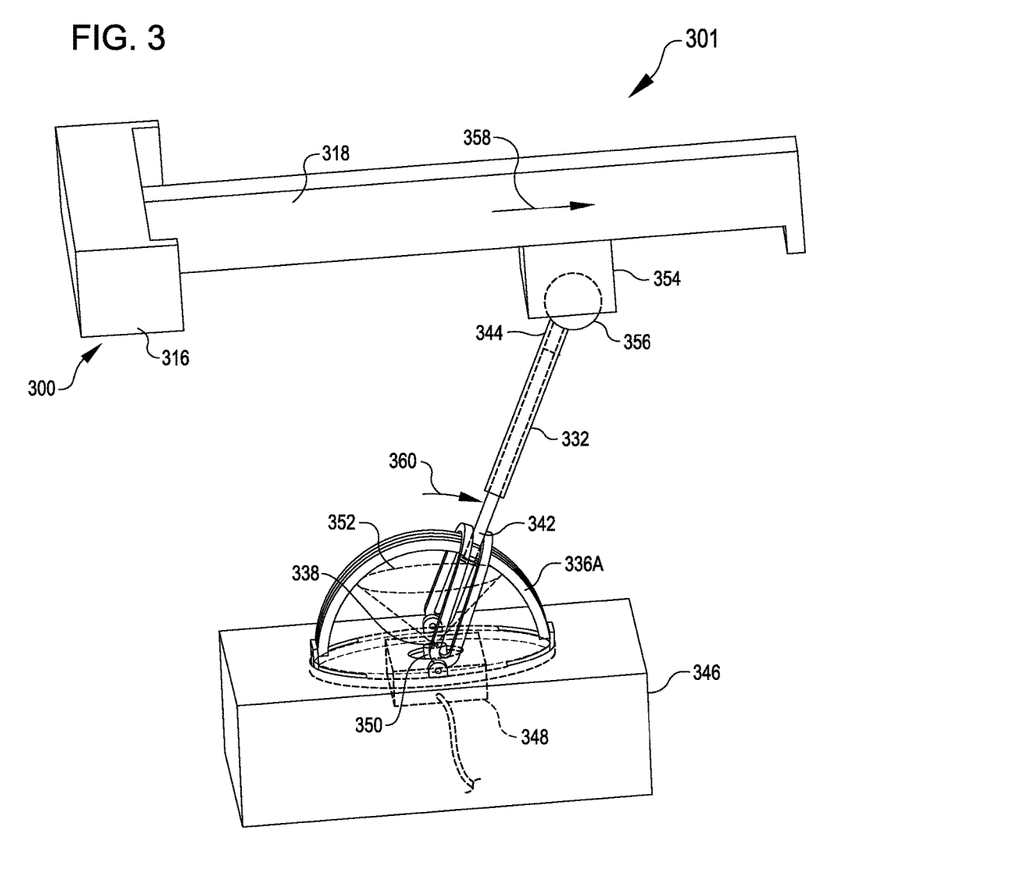
FIG. 3 is a side view illustrating a particular example of a system for translating positions and/or testing in accordance with various embodiments.

FIG. 3 is a side view illustrating a particular example of a system 301 for translating positions and/or testing. The system 301 depicted in FIG. 3 includes an actuator 300, a member 332, guides 336, a base 346, a first device 338, and a second device 340. The guides 336 include a first guide 336A and a second guide 336B. The guides 336 can each have a curved body. For example, the guides may be arcuate or semi-circular. The guides 336 overlap one another such that one is positioned outwardly of the other relative to the base 346, which can allow the guides to each pivot without interfering with one another.

The base 346 includes a first mount 348 that is configured for holding the first device 338. The first device in FIG. 3 is depicted as a laser-emitting device that is directed through a diffusing material 350 in order to generate a cone 352 of diffused laser light. Such a cone 352 may be useful for object detection purposes for robots, other movable objects, or other instances for which it may be useful to detect proximity or physical characteristics of objects nearby. The second device 340 in FIG. 3 is depicted as a laser-receiving device, e.g., which may be capable of obtaining readings (e.g., at different positions provided by the system 301) to provide information about an intensity or other characteristic of the light received from the laser-emitting device. Although the system 301 depicted in FIG. 3 is depicted with elements that may be useful for testing or calibrating a laser-based sensor, other options are also possible, including, but not limited to the different types of pairs of devices described above with respect to the fixed device 238 and the traveling device 240.

The actuator 300 is illustrated as a bi-axis actuator having a first linear actuator 316 and a second linear actuator 318. For ease of reference, these elements hereinafter may alternatively be referred to as a horizontal linear actuator 316 and a vertical actuator 318, although the actuator 300 need not necessarily only be capable of motion in the depicted horizontal and vertical directions.

In FIG. 3, the vertical linear actuator 318 is shown coupled with a housing 354 that contains a ball joint 356 that is coupled with the second end 344 of the member 332, while the first end 342 of the member 332 is engaged in or by the first guide 336A. Thus, in operation, as the linear actuator 318 moves the housing 354 in a vertical direction, e.g., as illustrated by arrow 358, the first end 342 of the member 332 can move along the first guide 336A in an arcing direction as illustrated by arrow 360.

Figure 4:
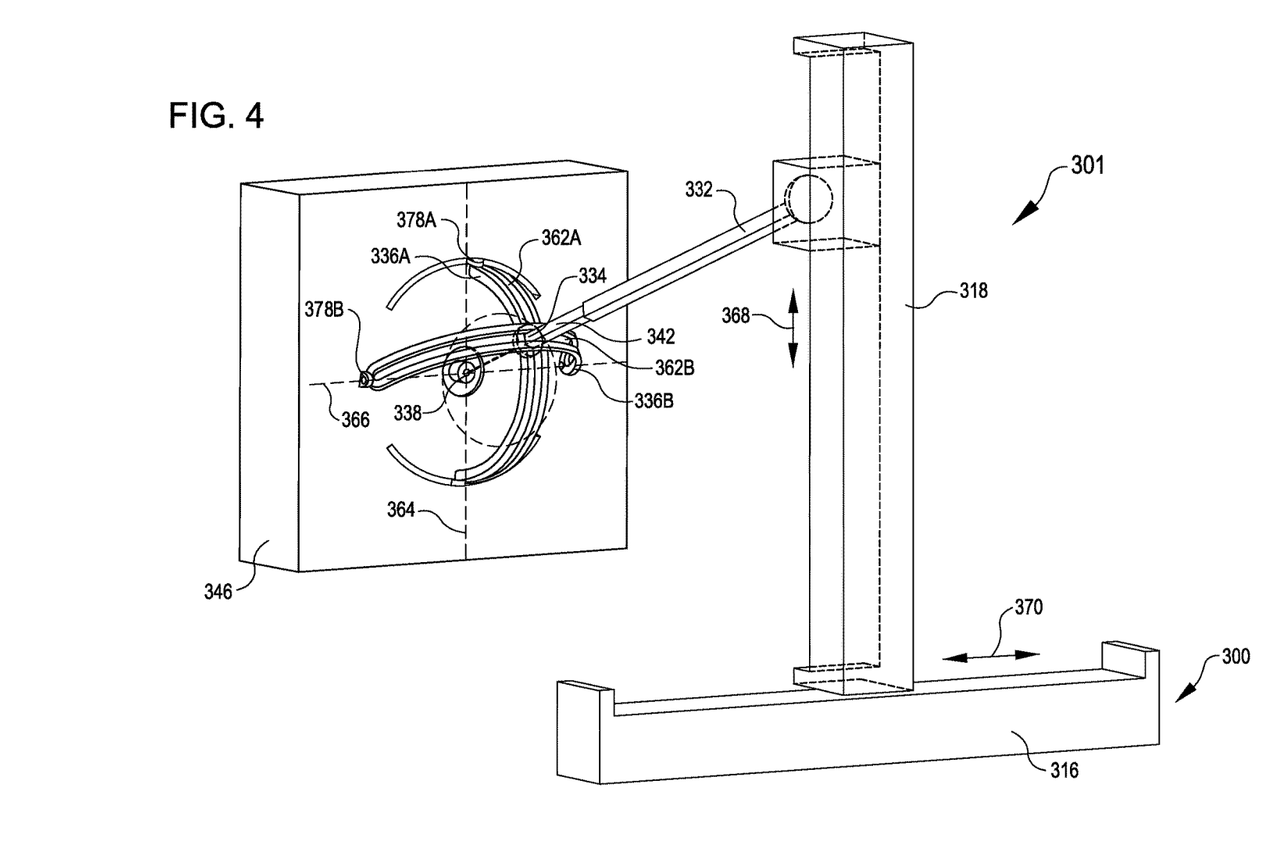
FIG. 4 is a top perspective view of the system of FIG. 3 in accordance with various embodiments.

FIG. 4 is a top perspective view of the system 301 of FIG. 3. Various details of the system 301 may be more easily seen in FIG. 4 than in FIG. 3. For example, in FIG. 4 hinges 378A and 378B are identified that respectively couple the first guide 336A and the second guide 336B to the base 346. The hinges 378 can permit the first guide 336A to pivot about a first axis of rotation 364A and permit the second guide 336B to pivot about a second axis of rotation 366. The first axis of rotation 364A and the second axis of rotation 366 are depicted perpendicular to one another in FIG. 4, although other options are possible, including, but not limited to those described with respect to the track 380 discussed below with reference to FIG. 5.

In FIG. 4, a first slot 362A can also be seen extending along the length of the first guide 336A, and a second slot 362B is shown extending along the length of the second guide 336B. The chassis 334 (which corresponds to a portion of the member 332 at or adjacent to the first end 342 in FIG. 4) is received through the first slot 362A and the second slot 362B. Thus, in addition to being able to move along the first guide 336A in response to vertical movement along the vertical linear actuator 318 as described in FIG. 3, the chassis 334 may additionally move along the second guide 336B in response to movement provided by the horizontal linear actuator 316. Horizontal movement (e.g., along the horizontal direction depicted by the double headed arrow 370) caused by the horizontal linear actuator 316 may cause the chassis 334 to push or pull against the sides of the first slot 362A of the first guide 336A and cause the first guide 336A to pivot about the first axis of rotation 364 while the chassis 334 also slides in the second slot 362B of the second guide 336B. Similarly, vertical movement (e.g., along the vertical direction depicted by the double headed arrow 368) provided by the vertical linear actuator 318 may cause the chassis 334 to exert a force on the sides of the second slot 362B of the second guide 336B to cause pivoting about the second axis of rotation 366 while the chassis 334 also slides within the first slot 362A of the first guide 336A. In this fashion, the guides 336 can constrain movement of the chassis 334 among radial positions or spherical positions defined around the fixed device 338 at a fixed radial distance corresponding to a spherical cap.

Figure 5:
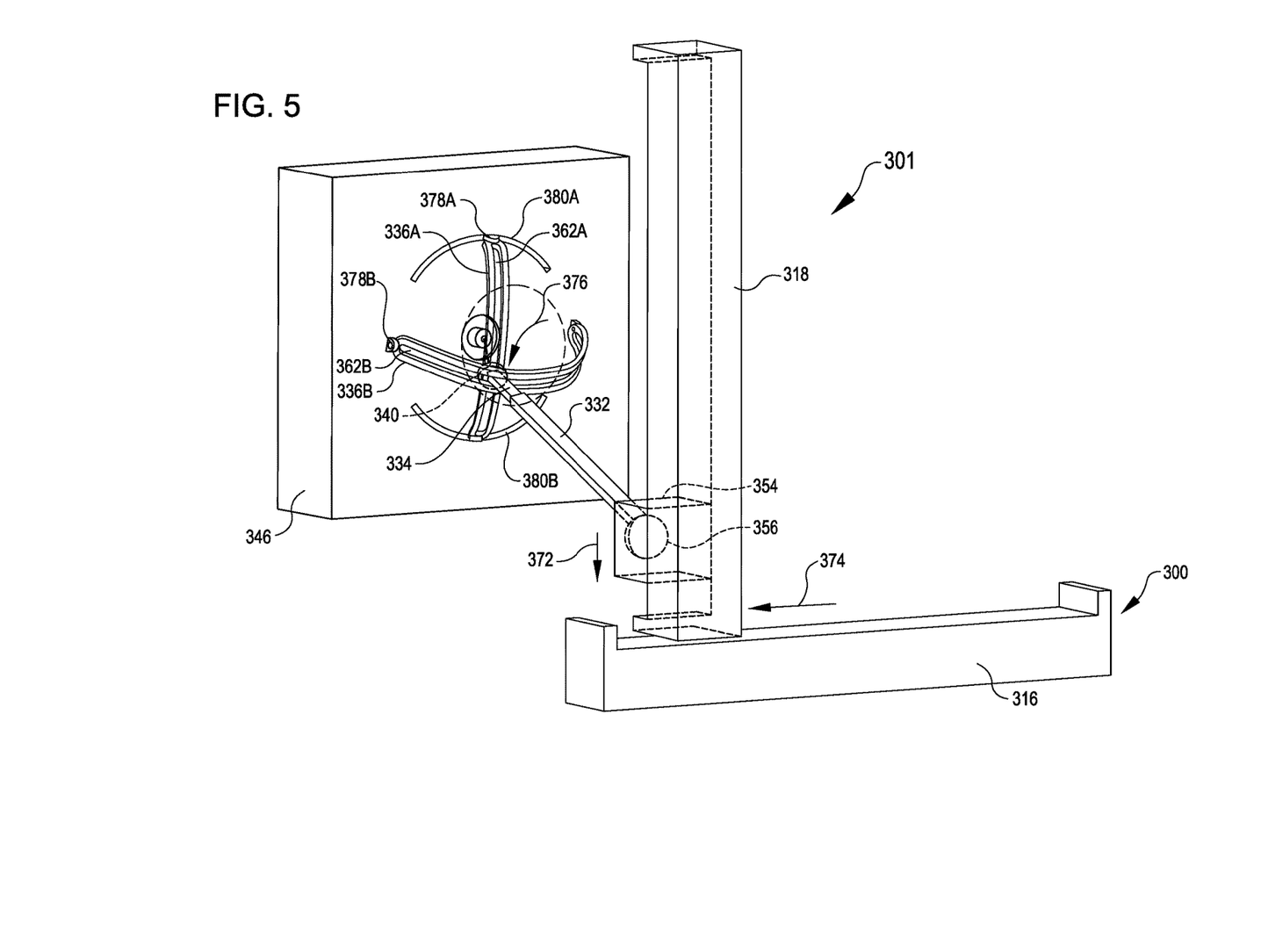
FIG. 5 illustrates the system from FIG. 4 in a state in which certain elements have been moved to new positions in accordance with various embodiments.

FIG. 5 illustrates the system 301 in a state in which elements have moved to respective new planar and translated spherical positions. For example, if the vertical linear actuator 318 moves the housing 354 of the ball joint 356 by a certain amount in the vertical direction (e.g., depicted by arrow 372) and the horizontal actuator 316 in tandem provides a certain amount of horizontal translation (e.g., as depicted by arrow 374), a combined arcing movement (e.g., as illustrated by curved arrow 376) may result with respect to the movement of the chassis 334 (and/or the second device 340 if coupled or mounted therewith).

The member 332 depicted in FIGS. 4 and 5 has a non-rounded cross-sectional shape. Such a non-rounded cross-section may constrain the chassis 334 to move in translating motion through the slots 362 and prevent or reduce an amount of twisting or other rotation of the member 332 within the slots 362. In various embodiments, preventing rotation within the slots 362 may cause the second device 340 to remain directly facing the first device 338 without changing an orientation that might affect data capture.

The member 332 is depicted in FIGS. 3-5 as being a telescoping rod. Such a construction may provide advantages such as those described above with respect to FIG. 2 regarding the member 332 being a variable length member. For example, the member 332 being variable length may allow the member 332 to extend and retract so as to remain spanning from the reference spherical cap 104 to the reference plane 102 as the chassis 334 moves along the guides 336.

As may best be seen in FIG. 5, the hinges 378A are shown as being received in a track 380. The track is shown having parts 380A and 380B to receive opposite ends of the first guide 336A. The track 380, for example, may correspond to a rail or a recess in which the hinges 378A may slide in order to allow the first guide 336A to twist about the base 346. For example, such twisting may be oriented along an axis perpendicular to both the axes of rotation 366 and 364 of FIG. 4. Such twisting action provided by the track 380 may allow an additional degree of freedom that may be useful for allowing the guides 336 to freely move and not bind when responding to motion conveyed by the member 332 from the actuator 300.

FIGS. 3, 4, and 5 are described with respect to the actuator 300 being positioned above the base 346. However, other orientations are also feasible such as the base 346 and actuator 300 being positioned opposite one another, for example, both being arranged vertically relative to a reference floor as opposed to horizontally over a reference floor by which both are supported.

Figure 6:
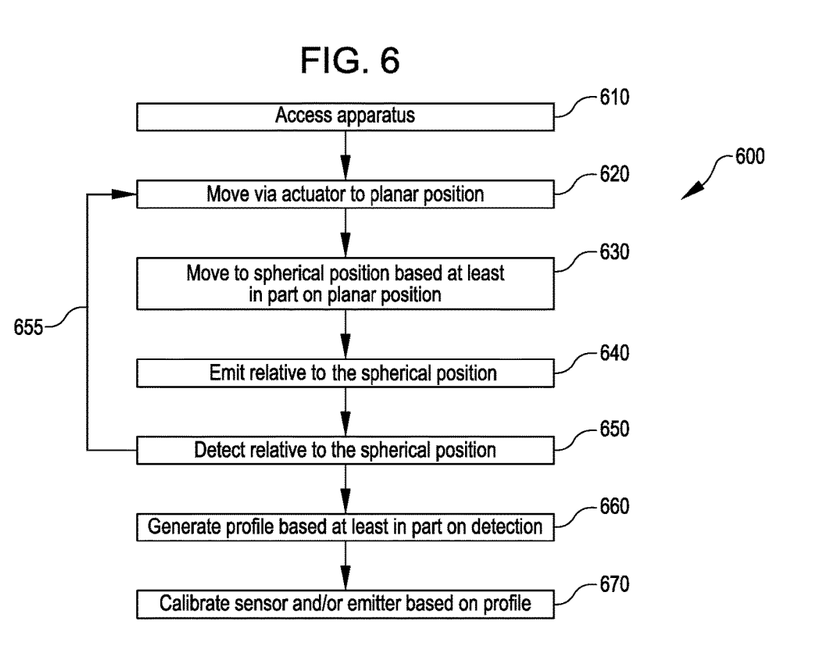
FIG. 6 is a flow chart illustrating a process that may be performed according to certain embodiments herein.

FIG. 6 is a flow chart illustrating a process that may be performed according to certain embodiments herein. Some or all of the process 600 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The process 600 at operation 610 includes accessing an apparatus. This may include accessing an apparatus having features such as described elsewhere herein. For example, the apparatus may include an appropriate actuator 100, 200, or 300 for moving within a plane 102 and an appropriate member 232 or 332 for engaging suitable guides 236 or 336 to cause motion along a spherical cap 104 by a traveling device 240, 340 relative to a fixed device 238, 338. In some embodiments, the operation 610 can include accessing the suitable actuator 100, 200, or 300 of such a device in order to impart a motion to reach a two-dimensional planar position 106 that can be converted by the physical structure of the apparatus into a spherical position 108.

The process 600 at operation 620 can include moving via an actuator to a planar position. This can include using a suitable actuator 100, 200, or 300 to reach a planar position 106 on a plane 102 such as described above.

The process 600 at operation 630 can include moving to a spherical position based at least in part on the planar position. For example, this may correspond to the structure of the apparatus described herein acting a translator from the planar position to the spherical position as a result of the arrangement of the constituent elements.

The process 600 at operation 640 can include emitting relative to the spherical position. This may include emitting from or toward (or to) the spherical position. For example, this may include the fixed device 238, 338 emitting toward or to the travelling device 240, 340 at the spherical position or vice versa (e.g., so that the travelling device 240, 340 emits from the spherical position and toward or to the fixed device 238, 338).

The process 600 at operation 650 can include detecting relative to the spherical position. For example, if the fixed device 238, 338 is emitting, the operation at 650 can include receiving the emission with the travelling device 240, 340. Alternatively, if the emission is provided from the traveling device 240, 340, the operation at 650 may include detecting via the fixed device 238, 338.

The process 600 at operation 655 can include iterating the operations 620, 630, 640, and 650. For example, after moving to a first planar position (at 620) and triggering or otherwise causing a move to a corresponding first spherical position (at 630) relative to which an emission and detection are performed and obtained (respectively at 640 and 650), the process 600 can iterate at 655 such that the actuator moves to a second planar position at 620. This second instance of the operation at 620 can cause movement to a second spherical position based at least in part on that second planar position movement (at a second instance of the operation at 630). This may be followed by triggering a second round of emission and detection relative to the second spherical position (at second instances of 640 and 650). The operation at 655, for example, may be incremented through different positions provided by the actuator. In an illustrative example, the operation at 655 can include incrementing an X-axis by one amount and causing the respective emission and detection, then incrementing the X-axis by the one amount again and causing further respective emission and detection, followed by incrementing the Y-axis by a suitable amount, and then repeating another set of increments along the X-axis with intervening emission and detection at each point in order to obtain an extensive data set.

The process 600 at operation 660 can include generating a profile based at least in part on the detection provided by operation 650 or the various detections provided at multiple instances of the operation 650 during iterating at 665. For example, based on a variety of X- and Y-coordinates through which the actuator has been incremented to cover a set of points in the plane, the values of various emissions and detections can be provided along a corresponding set of spherical positions, which may provide a robust profile of signal strength or other characteristic along a hemispherical or other spherical cap relative to the fixed device in a manner than can be used for a later improving functionality of the fixed device and/or the traveling device or corollaries thereof.

The process 600 at 670 can be include calibrating a sensor and/or an emitter based on the profile. The profile developed at 660 can be used in the operation at 670 to improve operation of related components. In one illustrative example, the sensor that is calibrated may be a sensor configured for object detection relative to a mobile drive unit. For example, the sensor in this example may be a proximity sensor borne by the mobile drive unit and which receives and interprets emitted laser light that is diffused into a cone and reflected by objects proximate to the mobile drive unit. In this example, the proximity sensor can be calibrated based on information obtained by an apparatus, for example, such as that depicted and described in FIGS. 3-5. However, embodiments herein are not so limited and may correspond to any other sensor or emitter, including, but not limited to, others explicitly described herein.

Figure 7:
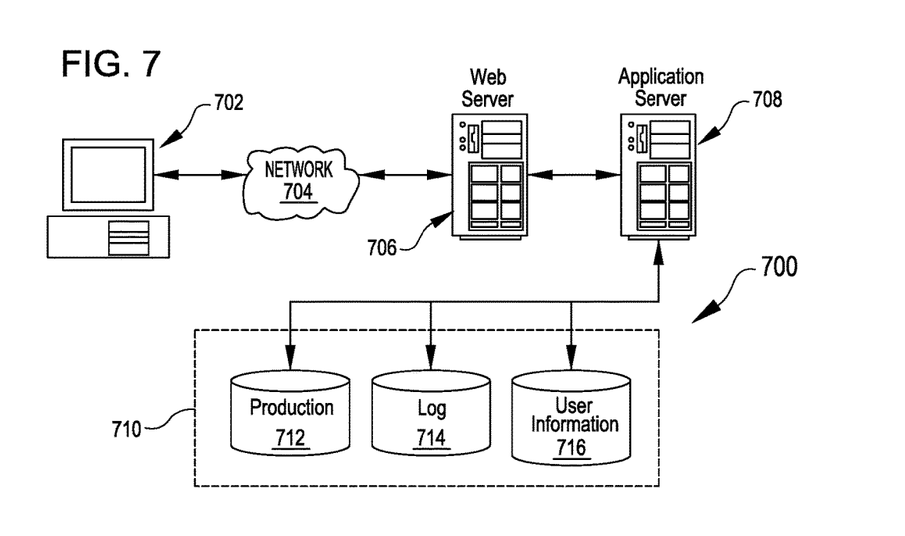
FIG. 7 illustrates an environment in which various embodiments can be implemented.

FIG. 7 illustrates aspects of an example environment 700 for implementing aspects in accordance with various embodiments. As will be appreciated, although a Web-based environment is used for purposes of explanation, different environments may be used, as appropriate, to implement various embodiments. The environment includes an electronic client device 702, which can include any appropriate device operable to send and receive requests, messages, or information over an appropriate network 704 and convey information back to a user of the device. Examples of such client devices include personal computers, cell phones, handheld messaging devices, laptop computers, set-top boxes, personal data assistants, electronic book readers, and the like. The network can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. In this example, the network includes the Internet, as the environment includes a Web server 706 for receiving requests and serving content in response thereto, although for other networks an alternative device serving a similar purpose could be used as would be apparent to one of ordinary skill in the art.

The illustrative environment includes at least one application server 708 and a data store 710. It should be understood that there can be several application servers, layers, or other elements, processes, or components, which may be chained or otherwise configured, which can interact to perform tasks such as obtaining data from an appropriate data store. As used herein the term "data store" refers to any device or combination of devices capable of storing, accessing, and retrieving data, which may include any combination and number of data servers, databases, data storage devices, and data storage media, in any standard, distributed, or clustered environment. The application server can include any appropriate hardware and software for integrating with the data store as needed to execute aspects of one or more applications for the client device, handling a majority of the data access and business logic for an application. The application server provides access control services in cooperation with the data store and is able to generate content such as text, graphics, audio, and/or video to be transferred to the user, which may be served to the user by the Web server in the form of HyperText Markup Language ("HTML"), Extensible Markup Language ("XML"), or another appropriate structured language in this example. The handling of all requests and responses, as well as the delivery of content between the client device 702 and the application server 708, can be handled by the Web server. It should be understood that the Web and application servers are not required and are merely example components, as structured code discussed herein can be executed on any appropriate device or host machine as discussed elsewhere herein.

The data store 710 can include several separate data tables, databases or other data storage mechanisms and media for storing data relating to a particular aspect. For example, the data store illustrated includes mechanisms for storing production data 712 and user information 716, which can be used to serve content for the production side. The data store also is shown to include a mechanism for storing log data 714, which can be used for reporting, analysis, or other such purposes. It should be understood that there can be many other aspects that may need to be stored in the data store, such as for page image information and to access right information, which can be stored in any of the above listed mechanisms as appropriate or in additional mechanisms in the data store 710. The data store 710 is operable, through logic associated therewith, to receive instructions from the application server 708 and obtain, update or otherwise process data in response thereto. In one example, a user might submit a search request for a certain type of item. In this case, the data store might access the user information to verify the identity of the user and can access the catalog detail information to obtain information about items of that type. The information then can be returned to the user, such as in a results listing on a Web page that the user is able to view via a browser on the user device 702. Information for a particular item of interest can be viewed in a dedicated page or window of the browser.

Each server typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environtext in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 7. Thus, the depiction of the system 700 in FIG. 7 should be taken as being illustrative in nature and not limiting to the scope of the disclosure.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as Transmission Control Protocol/Internet Protocol ("TCP/IP"), Open System Interconnection ("OSI"), File Transfer Protocol ("FTP"), Universal Plug and Play ("UpnP"), Network File System ("NFS"), Common Internet File System ("CIFS"), and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including Hypertext Transfer Protocol ("HTTP") servers, FTP servers, Common Gateway Interface ("CGI") servers, data servers, Java servers, and business application servers. The server(s) also may be capable of executing programs or scripts in response to requests from user devices, such as by executing one or more Web applications that may be implemented as one or more scripts or programs written in any programming language, such as Java®, C, C#, or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired)), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory ("EEPROM"), flash memory or other memory technology, Compact Disc Read-Only Memory ("CD-ROM"), digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:
1. A method, comprising:
　accessing an apparatus configured for testing laser emission along a reference spherical cap, the apparatus comprising:
　　a base;
　　a laser-emitting device mounted to the base;

a first guide pivotally coupled with the base and comprising a first semi-circular body defining a first slot there through;

a second guide pivotally coupled with the base and comprising a second semi-circular body defining a second slot there through, the second guide overlapping the first guide and positioned outwardly from the first guide relative to the base;

a chassis received through the first slot and the second slot so as to be configured for sliding along the first guide and the second guide;

a laser-detecting device mounted to the chassis so as to be configured for movement between a first set of points defining the reference spherical cap;

a variable-length member having a first end and a second end, the first end coupled with the chassis; and a bi-axis actuator coupled with the second end of the variable-length member so as to be configured for movement of the second end of the variable-length member between a second set of points defining a reference plane;

moving the second end of the variable-length member via the bi-axis actuator to a first planar position on the reference plane and thus causing the laser-detecting device to move to a first spherical position on the reference spherical cap;

emitting a first laser emission from the laser-emitting device toward the first spherical position; and detecting the first laser emission by the laser-detecting device at the first spherical position to obtain a first laser reading.

2. The method of claim 1, further comprising:

moving the second end of the variable-length member via the bi-axis actuator to a second planar position on the reference plane and thus causing the laser-detecting device to move to a second spherical position on the reference spherical cap;

emitting a second laser emission from the laser-emitting device toward the second spherical position;

detecting the second laser emission by the laser-detecting device at the second spherical position to obtain a second laser reading; and generating a profile of a strength of the laser-emitting device along the reference spherical cap based at least in part on the first laser reading and the second laser reading.

3. The method of claim 2, further comprising calibrating a sensor based at least in part on the profile, wherein the sensor is configured for object detection relative to a mobile drive unit.

4. The method of claim 1, wherein the moving the second end of the variable-length member via the bi-axis actuator to the first planar position on the reference plane comprises moving the bi-axis actuator along at least one of:

a first axis of the bi-axis actuator; or a second axis of the bi-axis actuator that is perpendicular to the first axis.

5. An apparatus, comprising:

a base;

a first device from a pair of devices, the pair of devices comprising an emitting device and a corresponding receiving device configured to detect an emission from the emitting device, the first device mounted to the base;

a first guide pivotally coupled with the base and comprising a first arcuate body;

a second guide pivotally coupled with the base and comprising a second arcuate body, the second guide overlapping the first guide and positioned outwardly from the first guide relative to the base;

a chassis received by the first guide and the second guide so as to be configured for sliding along the first guide and the second guide;

a second device from the pair of devices, the second device mounted to the chassis so as to be configured for movement between a first set of points defining the reference spherical cap;

a variable-length member having a first end and a second end, the first end coupled with the chassis; and an actuator coupled with the second end of the variable-length member and configured for movement of the second end of the variable-length member between a second set of points defining a reference plane so as to cause movement of the chassis among the first set of points defining the reference spherical cap.

6. The apparatus of claim 5, wherein the actuator comprises a bi-axis actuator.

7. The apparatus of claim 6, wherein the first arcuate body comprises a first semi-circular body; and wherein the second arcuate body comprises a second semi-circular body.

8. The apparatus of claim 7, wherein the variable-length member extends and retracts so as to remain spanning from the reference spherical cap to the reference plane as the chassis moves along the first guide and the second guide;

wherein the first semi-circular body defines a first slot there through;

wherein the second semi-circular body defines a second slot there through; and wherein the chassis is received through the first slot and the second slot so as to be configured for sliding along the first guide and the second guide.

9. The apparatus of claim 8, wherein the first device is a laser-emitting device and the second device is a laser-detecting device.

10. The apparatus of claim 9, further comprising a diffusing element configured to distribute laser light from the laser-emitting device into a cone, wherein the laser-detecting device is configured to detect an intensity of laser light from the cone.

11. The apparatus of claim 5, wherein the pair of devices comprises:

a speaker and a microphone;

a sound emitter and a sound receiver;

a non-laser heat source and a heat detector; or an emitter of non-visible electromagnetic radiation and a receiver of the non-visible electromagnetic radiation.

12. The apparatus of claim 5, wherein the actuator comprises:

a robotic arm; or an assembly comprising a length-adjustable actuator and an angle-adjustable actuator.

* * * * *